United States Patent [19]

Ishihara et al.

[11] 4,337,372

[45] Jun. 29, 1982

[54] METHOD FOR THE CIS TO TRANS ISOMERIZATION OF AN ALKENOL

[75] Inventors: Toshinobu Ishihara; Akira Yamamoto; Kenichi Taguchi, all of Joetsu, Japan

[73] Assignee: Shin-Etsu Chemical Company Limited, Tokyo, Japan

[21] Appl. No.: 266,615

[22] Filed: May 22, 1981

[30] Foreign Application Priority Data

May 26, 1980 [JP] Japan .................................. 55-69723

[51] Int. Cl.$^3$ .............................................. C07C 29/56
[52] U.S. Cl. .................................................. 568/906
[58] Field of Search ........................................ 568/906

[56] References Cited

U.S. PATENT DOCUMENTS 3,449,384  6/1969  Ender ................................ 568/906

*Primary Examiner*—Joseph E. Evans
*Attorney, Agent, or Firm*—Toren, McGeady & Stanger

[57] ABSTRACT

The invention provides a novel method for the cis to trans isomerization of an alkenyl alcohol in a very simple process. The inventive method comprises heating the cis-isomer at a temperature of, for example, 150° to 200° C. in the presence of selenium metal in a powdery form with agitation.

4 Claims, No Drawings

METHOD FOR THE CIS TO TRANS ISOMERIZATION OF AN ALKENOL

BACKGROUND OF THE INVENTION

The present invention relates to a method for the isomerization of a cis-alkenol compound to a corresponding trans-alkenol compound.

In recent years, there has been proposed a promising method for the extermination of noxious insects such as those belonging to the Lepidoptera, e.g. butterflies and moths, utilizing a so-called sexual pheromone compound which is excreted by a particular insect of a sex and attracts very strongly the insects of the same species of another sex even in an extremely low concentration. Many of the sexual pheromone compounds of the Lepidoptera has a chemical structure in which one or two of the ethylenic double bonds are included in a straight chain molecule. Most of these compounds are the cis-isomers in the geometrical isomerism relative to the double bonds but some of the sexual pheromone compounds are a mixture of the cis- and the trans-isomers.

For example, the sexual pheromone compound of nashihimeshinkuiga (oriental fruit moth) is a mixture of the cis- and the trans-isomers of 9-dodecenyl acetate in a proportion of 93:7. Further, the sexual pheromone compound of tsuzurimonhamaki is a 1:1 mixture of cis- and trans-11-tetradecenyl acetates.

Usually, there is no particular problem in the synthetic preparation of the cis-isomers of the above described type since catalytic partial hydrogenation of an acetylenically unsaturated compound gives the cis-isomer of the corresponding ethylenically unsaturated compound in a much larger yield than the trans-isomer. When a mixture of the cis- and the trans-isomers of an ethylenically unsaturated compound is desired, however, no industrially advantageous method is known to obtain such a mixture with a desired ratio of the trans-isomer to the cis-isomer since the content of the trans-isomer in the mixture can rarely exceed 2 to 5% even under the most favorable conditions for the formation of the trans-isomer. When a higher content of the trans-isomer is desired relative to the cis-isomer, therefore, it is a usual practice that the trans-isomer is synthesized separately and mixed with the cis-isomer in a desired proportion although such a method is industrially not practicable since no advantageous method is known for the synthesis of the trans-isomer alone.

Thus, it has long been desired to develop an industrially advantageous method in which relatively easily available cis-isomers are isomerized into the corresponding trans-isomers in a simple process.

SUMMARY OF THE INVENTION

An object of the present invention is therefore to provide a novel and unique method for the isomerization of a cis-isomer of an ethylenically unsaturated organic compound into the corresponding trans-isomer. In particular, the present invention is directed to the isomerization of a cis-isomer of an ethylenically unsaturated aliphatic alcohol or cis-alkenol into the corresponding trans-isomer of the alkenol.

The method of the present invention comprises heating the cis-isomer of an alkenyl alcohol represented by the general formula

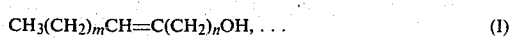

$$CH_3(CH_2)_m CH=\!=\!C(CH_2)_n OH, \ldots \quad (I)$$

in which m and n are each an integer from 1 to 10 inclusive, in the presence of selenium metal.

DETAILED DESCRIPTION OF THE PREFERRED EMBODIMENTS

The alkenyl alcohol compounds, of which the cis-isomer is subjected to the treatment according to the invention, as represented by the above given general formula (I) are exemplified by 3-hexenol, 3-butenol, 3-octenol, 6-nonenol and the like. The cis-isomers of these alkenyl alcohols are merely heated in the presence of selenium metal which is used preferably in a powdery form. The amount of the selenium metal to be added to the cis-isomer of the alkenyl alcohol is in the range from about 0.1 to about 5.0% by weight based on the cis-isomer of the alkenyl alcohol.

The temperature at which the starting cis-isomer is heated in the presence of selenium metal should be sufficiently high in order to obtain sufficiently high velocity of the isomerization reaction and usually the reaction is carried out at a temperature in the range from 150° to 200° C. The conversion of the cis-isomer to the trans-isomer by the isomerization increases so much as the reaction time is extended. Accordingly, the method of the present invention is applicable not only to a pure cis-isomer but also to a mixture of the cis-isomer and the trans-isomer to obtain a cis/trans mixture enriched in the content of the trans-isomer. Further, the proportion of the trans-isomer to the cis-isomer can freely be controlled by selecting the reaction temperature and the duration of the reaction so that a great practical advantage is obtained by the inventive method.

Following are the examples to illustrate the inventive method in further detail.

EXAMPLE 1

Into a flask of 500 ml capacity were introduced 200 g of 3-octen-1-ol, of which the contents of the cis- and the trans-isomers were 98% and 2%, respectively and selenium metal, and the mixture was agitated at 180° C. with periodical sampling of a small portion which was analyzed for the contents of the cis- and the trans-isomers to give the results shown below.

| Reaction time, minutes | Content of the cis-isomer, % | Content of the trans-isomer, % | Ratio of trans-isomer/cis-isomer |
| --- | --- | --- | --- |
| 0 | 98 | 2 | 0.02 |
| 30 | 81 | 19 | 0.23 |
| 50 | 64 | 36 | 0.56 |
| 70 | 54 | 46 | 0.85 |
| 90 | 36 | 64 | 1.78 |

EXAMPLE 2

The experimental procedure was substantially the same as in Example 1 except that the 3-octen-1-ol was replaced with 6-nonen-1-ol, of which the ratio of the trans-isomer to the cis-isomer was 0.02. After 60 minutes of the reaction undertaken with heating, the ratio of the trans-isomer to the cis-isomer increased to 2.33.

What is claimed is:

1. A method for the isomerization of a cis-isomer of an ethylenically unsaturated aliphatic alcohol represented by the general formula $$CH_3(CH_2)_mCH=CH(CH_2)_nOH$$

in which m and n are each an integer from 1 to 10 inclusive, into the trans-isomer which comprises heating the cis-isomer in the presence of selenium metal.

2. The method as claimed in claim 1 wherein the selenium metal is in a powdery form.

3. The method as claimed in claim 1 wherein the amount of the selenium metal is in the range from 0.1 to 5.0% by weight based on the amount of the cis-isomer.

4. The method as claimed in claim 1 wherein the temperature of heating is in the range from 150° to 200° C.